United States Patent
Grützmacher et al.

(10) Patent No.: US 7,230,137 B2
(45) Date of Patent: Jun. 12, 2007

(54) PROCESS FOR THE SYNTHESIS OF CYCLOORGANYLPHOSPHANES AND DI(ALKYLI METAL/ALKALINE EARTH METAL) OLIGOPHOSPHANEDIIDES

(75) Inventors: Hansjörg Grützmacher, Dielsdorf (CH); Jens Geier, Tsukuba (JP); Hartmut Schönberg, Kilchberg (CH); Markus Scherer, Beromünster (CH); Daniel Stein, Seelze (DE); Souâd Boulmaâz, Birsfelden (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 55 days.

(21) Appl. No.: 10/535,372

(22) PCT Filed: Nov. 24, 2003

(86) PCT No.: PCT/EP03/50873

§ 371 (c)(1),
(2), (4) Date: May 19, 2005

(87) PCT Pub. No.: WO2004/050668

PCT Pub. Date: Jun. 17, 2004

(65) Prior Publication Data

US 2005/0283027 A1 Dec. 22, 2005

(30) Foreign Application Priority Data

Dec. 4, 2002 (EP) .................................. 02406055

(51) Int. Cl.
*C07F 9/547* (2006.01)
(52) U.S. Cl. ........................................ 568/9
(58) Field of Classification Search .................... 568/9
See application file for complete search history.

(56) References Cited

U.S. PATENT DOCUMENTS 6,888,031 B1  5/2005 Leppard et al. ............... 568/14

OTHER PUBLICATIONS

Jutzi et al., Pentamethylcyclopentadienyl Substituted Diphosphene, Bicyclo[1.1.0]tetraphosphane Cyclotetraphosphane and cyclotriphosphanes from Dihalo(pentamethylcyclopentadienyl) phosphanes, Journal of Organometallic Chemistry, 1985, 287 (1), C5-C7.*
Rausch et al., The Synthesis of Metallaindene and Metalafluorene Compounds, Synthesis and Reactivity in Inorganic and Metal-Organic Chemistry, 1985, 15 (7), 923-943.*
Borm et al., Preparation of Three-Membered Phosphorus Containing Ring Ligands from Phosphinidene and Diphosphene Complexes, Journal of Organometallic Chemistry, 1986, 306 (1), 29-38.*
Ionkin et al., Investigation of the Dehalogenation reaction of (2,4-di-tert-butyl-6-methyiphenyl)dihalophosphine with Magnesium by Phosphorus-31 CIDNP Methods, Izvestiya Akademi Nauk, Seriya Khimicheskaya, 1992, 3, 726-730.*
Diemert et al., Organophosphorus Compounds. XXIII. Alkenyl Substituted Amino- or Halophosphines and Attempts to Trap Phosphinidene Intramolecuarly, Phosphorus and Sulfur and Related Elements, 1986, 26 (3), 307-320.*
Goerlich et al., Tris-1-Adamantylcyclotriphosphine and Tetrakis-1-Adamantylcyclotetraphosphine: Two Peradamantylated Examples from the Cyclopolyphosphine Series (RP)n, Zeitschrift Fuer Anorganische und Allgemeine Chemie, 1994, 620 (1), 173-176.*
Schisler et al., Synthesis, Properties and Structure and Reactivity of Sodium 2,3,4,5-Tetra-tert-Butylcyclopentaphosphanide, Phosphorus, Sulfur and Silicon, 2002, vol. 177, 1447-1450.*
F. Pass et al., Monatshefte Fur Chemie, vol. 90, (1959), pp. 148-156.
A. Hinke et al., Chemische Berichte, vol. 116, No. 5, (1983), pp. 3003-3010.
W. Henderson et al., Journal of the American Chemical Society, vol. 85, (1963), pp. 2462-2466.
A. Schisler et al., Phosphorus, Sulfur, and Silicon and the Related Elements, vol. 177, No. 6/7, (2002), pp. 1447-1450.
M. Baudler, Angewandte Chemie, vol. 21, (1982) pp. 492-512.
P. Bloomfield et al., Journal of Applied Chemistry, (1959), pp. 541-543.
N. Kuhn et al., Synthetic Methods of Organometallic and Inorganic Chemistry, vol. 4, (1997), pp. 76-79.
P. Jutzi et al., Synthetic Methods of Organometallic and Inorganic Chemistry, vol. 3, (1996), pp. 113-118.
M. Baudler et al., Chemical Reviews, American Chemical Society, vol. 93, (1983), pp. 1623-1667.

* cited by examiner

*Primary Examiner*—Thurman K. Page
*Assistant Examiner*—Chukwuma Nwaonicha
(74) *Attorney, Agent, or Firm*—Tyler A. Stevenson

(57) ABSTRACT

The invention relates to a process for the preparation of cycloorganylphosphanes of formula 1 $(R^1P)_n$ by reaction of dihalo(organyl)phosphanes of formula $R^1PHal_2$ with: a) activated zinc in an organic solvent, or with: b) an alkali metal or alkaline earth metal in a non-polar organic solvent in the presence of an activator, wherein $R^1$ is $C_1$–$C_{12}$alkyl; $C_3$–$C_{12}$ cycloalkyl, aryl or heteroaryl, Hal is F, Cl, Br or I, and n is a number from 3 to 20. The invention relates also to novel di(alkali metal/alkaline earth metal) oligophosphanediides and to the use thereof in the preparation of organophosphorus compounds.

11 Claims, No Drawings

PROCESS FOR THE SYNTHESIS OF CYCLOORGANYLPHOSPHANES AND DI(ALKYLI METAL/ALKALINE EARTH METAL) OLIGOPHOSPHANEDIIDES

The invention relates to a process for the synthesis of cycloorganylphosphanes and di(alkali metal/alkaline earth metal) oligophosphanediides from dihalo(organyl)phosphanes and to novel di(alkali metal/alkaline earth metal) oligophosphanediides and their use in the preparation of organophosphorus compounds.

Cycloorganylphosphanes $(RP)_n$ and metal phosphanides $M_x(P_nR_n)$ are valuable starting materials in the preparation of a large number of different classes of organophosphorus compounds.

Cycloorganylphosphanes can be prepared by dehalogenation of dihalo(organyl)phosphanes $RPHal_2$ using base metals, such as U, Na, K and Mg, in an ethereal solvent, such as tetrahydrofuran (THF) (A. Hinke, W. Kuchen, *Chem. Ber.* 1983, 116, 3003–3010).

In Monatshefte für Chemie, volume 90, 1959, pages 148–156, H. Schindibauer describes the preparation of phenylphosphine and tetraphenylcyclotetraphosphine by reacting phenylphosphine dichloride with metallic sodium.

The reaction of dichloro(organyl)phosphanes with the especially attractive dehalogenating agent zinc has not been examined in detail and, according to reports in the literature, it proceeds at satisfactory reaction rates and gives satisfactory yields only in the presence of trimethylphosphane, $PMe_3$, (S. Shah, J. D. Protasiewicz, *Coord. Chem. Rev.* 2000, 210, pages 181–201). In that reaction, compounds of the $RP=PMe_3$ type are isolated.

Good yields of cycloorganylphosphanes are obtained in a condensation reaction of a primary phosphane, $RPH_2$, and a dichloro(organyl)phosphane in the presence of a base, such as an amine (W M. A. Henderson, Jr., M. Epstein, F. S. Seichter, *J. Am. Chem. Soc.* 1963, 85, 2462).

The methods described for the preparation of cycloorganylphosphanes have a number of distinct disadvantages. The yields obtained in dehalogenation reactions are often only moderate. In addition, many of the described reactions are reproducible only with difficulty. These disadvantages are true especially of phenyl-substituted polyphosphanes which, however, in view of the ready availability of $PhPCl_2$, are of particular interest. The main disadvantage of the condensation method resides in the use of primary phosphanes, $RPH_2$, which are often pyrophoric and toxic.

It is known that metal phosphanides can be prepared from a dihalo(organyl)phosphane, $RPHl_2$, and a metal M (M=alkali metal or alkaline earth metal), preferably lithium, in an ethereal solvent, preferably tetrahydrofuran (THF) or dimethoxyethane (DME) (K. Issleib, *Z. Chem.* 1962, 2, 163–173).

It is also known that polyphosphanes $[RP]_n$ (R=organic radical, n=3–∞) react with reducing metals M in an ethereal solvent to form metal phosphanides $M_x(P_nR_n)$. Such a reaction is described, for example, in: ((a) J. W. B. Reesor, G. F. Wright, *J. Or. Chem.* 1957, 22, 385–387; (b) W. Kuchen, H. Buchwald, *Chem. Ber.* 1958, 91, 2296; (c) K. Issleib, K. Krech, *Chem. Ber.* 1966, 99, 1310–1314; (d) P. R. Hoffman, K. G. Caulton, *J. Am. Chem. Soc.* 1975, 97, 6370–6374).

It is furthermore known that polyphosphanes $[RP]_n$ react with metal phosphanides $M_2(PR^1)$ or with $M(PR^1{}_2)$ in ethereal solvents to form metal (oligophosphanides) $M_m[PR^1{}_k(RP)_{n-1}PR]$ (m=1, k=2; m=2, k=1) (K. Issleib, F. Krech, *J. prakt. Chem.* 1969, 311, 464).

A distinct disadvantage of such methods of synthesis is the use of a very aggressive reaction medium, which consists of an ether and of an alkali metal having a strong reducing action. Such mixtures are potentially highly hazardous. In particular, the strongly basic metal phosphanides decompose the ethers employed as solvents, forming alcoholates and readily volatile hydrocarbons, such as ethylene. The risk is generally that, in the event of contact with oxygen, highly explosive peroxides will be formed.

The object of the invention was to provide a less dangerous, simple, selective and efficient method of synthesising cycloorganylphosphanes and di(alkali metal/alkaline earth metal) oligophosphanediides.

The invention accordingly relates to a process for the preparation of cycloorganylphosphanes of formula I $(R^1P)_n$ by reaction of dihalo(organyl)phosphanes of formula $R^1PHal_2$, wherein
$R^1$ is $C_1$–$C_{12}$alkyl; $C_3$–$C_{12}$cycloalkyl, aryl or heteroaryl,
Hal is F, Cl, Br or I, and
n is a number from 3 to 20, with
a) activated zinc in an organic solvent, or with
b) an alkali metal or alkaline earth metal in a non-polar organic solvent in the presence of an activator selected from the group consisting of ethers and polyethers, amines and polyamines, aromatic N-heterocycles and carbonic acid derivatives, wherein the ratio by volume of non-polar solvent to activator is from 10:0.1 to 10:5.

Suitable aryl radicals include those which have a carbocyclic structure having from 6 to 24 structural atoms, such as, preferably, phenyl, naphthyl, biphenyl, binaphthyl, phenanthryl and anthryl.

Suitable heteroaryl radicals are those which have a heterocarbocyclic structure having from 5 to 24 structural atoms in which none, one, two or three of the structural atoms in each ring are hetero atoms; in the entire molecule, however, at least one structural atom is a hetero atom. The hetero atom is an atom from the group consisting of nitrogen, sulfur and oxygen, examples of heteroaryl radicals being, preferably, pyridyl, oxazolyl, thienyl, benzofuranyl, benzothiophenyl, dibenzofuranyl, dibenzothiophenyl, furyl, indolyl, pyridazinyl, pyrazinyl, imidazolyl, pyrimidinyl and quinolinyl.

The aryl radicals or heteroaryl radicals may also be substituted by up to five identical or different substituents per ring. The substituents are from the group consisting of fluorine, chlorine, nitro, cyano, free or protected formyl, hydroxy, $C_1$–$C_{12}$alkyl, $C_1$–$C_{12}$haloalkyl, $C_1$–$C_{12}$alkoxy, $C_1$–$C_{12}$haloalkoxy, $C_3$–$C_{12}$cycloalkyl, $C_6$–$C_{24}$aryl, for example phenyl, $C_6$–$C_{24}$arylalkyl, for example benzyl, di($C_1$–$C_{12}$alkyl)amino, ($C_1$–$C_{12}$alkyl)amino, $CO(C_1$–$C_{12}$alkyl), $OCO(C_1$–$C_{12}$alkyl), $N(C_1$–$C_6$alkyl)CO ($C_1$–$C_{12}$alkyl), $CO(C_6$–$C_{24}$aryl), $OCO(C_6$–$C_{24}$aryl), $N(C_1$–$C_6$alkyl)CO($C_6$–$C_{24}$aryl), $COO$—$(C_1$–$C_{12})$alkyl, $COO$—$(C_6$–$C_{24})$aryl and $CON(C_1$–$C_{12}$alkyl).

Suitable $C_1$–$C_{12}$alkyl groups include, for example, methyl, ethyl, propyl, isopropyl, butyl, sec- and tert-butyl, pentyl and hexyl.

Suitable $C_3$–$C_{12}$cycloalkyl groups include, for example, cyclopropyl, cyclobutyl, cyclopentyl, cyclohexyl, cycloheptyl, cyclooctyl and the like.

The solvents and solvent mixtures suitable for process step (a) are listed under A) to F).

A) Ethereal solvents, for example those having the composition $R^2$—O—$R^3$ or $R^2$—O—$[(CH_2$—$CH_2)$—$O]_n$—$R^3$.

The radicals $R^2$ and $R^3$ may be identical or different They are from the group consisting of $C_1$–$C_{12}$alkyl, $C_1$–$C_{12}$alkoxy, $C_3$–$C_{12}$cycloalkyl, $C_6$–$C_{24}$aryl, for example phenyl, $C_6$–$C_{24}$arylalkyl, for example benzyl, $CO(C_1$–$C_{12}$alkyl), $CO(C_6$–$C_{24}$aryl), $CON(C_1$–$C_{12}$alkyl)$_2$, $CON(C_6$–$C_{24}$aryl)$_2$ and $CON(C_1$–$C_{12}$alkyl)($C_6$–$C_{24}$aryl). The substituents $R^2$ and $R^3$ may also be a heteroaryl radical that has a heterocarbocyclic structure having from 5 to 24 structural atoms in which none, one, two or three of the structural atoms in each ring are hetero atoms; in the entire molecule, however, at least one structural atom is a hetero atom. The hetero atom is from the group consisting of nitrogen, sulfur and oxygen, examples of heteroaryl radicals being, preferably, pyridyl, oxazolyl, thienyl, benzofuranyl, benzothiophenyl, dibenzofuranyl, dibenzothiophenyl, furyl, indolyl, pyridazinyl, pyrazinyl, imidazolyl, pyrimidinyl and quinolinyl. The radicals $R^2$ and $R^3$ may also be an alkylene bridge —$[CR_2]_n$— wherein n=from 1 to 12 and R is a radical as defined above, cyclic ethers thus being formed. In addition, any mixture of such solvents is suitable as the reaction medium.

Preferred ethereal solvents are tetrahydrofuran, dioxane, dimethyl ether, diethyl ether, di(isopropyl) ether, methyl (tert-butyl) ether, 1,2-dimethoxyethane (DME). Preferred glycolic solvents $R^2$—O—$[(CH_2$—$CH_2)$—$O]_n$—$R^3$ are diethylene glycol dimethyl ether, triethylene glycol dimethyl ether and tetraethylene glycol dimethyl ether.

B) Amines, for example those having the composition $R^4R^5R^6N$ and $R^4R^5N$—$[(CH_2$—$CH_2)$—$NR^4]_n$—$R^5$ wherein the radicals $R^4$, $R^5$ and $R^6$ may in each case be identical or different. They are from the group consisting of H, $C_1$–$C_{12}$alkyl, $C_1$–$C_{12}$alkoxy, $C_3$–$C_{12}$cycloalkyl, $C_6$–$C_{24}$aryl, for example phenyl, $C_6$–$C_{24}$arylalkyl, for example benzyl, $CO(C_1$–$C_{12}$alkyl), $CO(C_6$–$C_{24}$aryl), $CON(C_1$–$C_{12}$alkyl)$_2$, $CON(C_6$–$C_{24}$aryl)$_2$ and $CON(C_1$–$C_{12}$alkyl)($C_6$–$C_{24}$aryl). The substituents $R^4$ to $R^6$ may also be a heteroaryl radical that has a heterocarbocyclic structure having from 5 to 24 structural atoms in which none, one, two or three of the structural atoms in each ring are hetero atoms; in the entire molecule, however, at least one structural atom is a hetero atom. The hetero atom is from the group consisting of nitrogen, sulfur and oxygen, examples of heteroaryl radicals being, preferably, pyridyl, oxazolyl, thienyl, benzofuranyl, benzothiophenyl, dibenzofuranyl, dibenzothiophenyl, furyl, indolyl, pyridazinyl, pyrazinyl, imidazolyl, pyrimidinyl and quinolinyl. The radicals $R^4$, $R^5$ and $R^6$ may also be an alkylene bridge —$[CR_2]_n$— wherein n=from 1 to 12 and R is a radical as defined above, cyclic amines thus being formed. In addition, any mixture of such solvents is suitable as the reaction medium.

Preferred aminic solvents are triethylamine, butylamine, dibutylamine, tributylamine, morpholine, piperidine, N-methylmorpholine, N-methylpiperidine, N,N,N',N'-tetramethylethylenediamine (TMEDA), pentamethyldiethylenetriamine (PMDETA), hexamethyltriethylenetetramine, diethylenetriamine, triethylenetetramine.

C) Solvents that carry both ether groups and amino groups are, for example, monoethanolamine, diethanolamine, triethanolamine, propanolamines and O—$C_1$–$C_{12}$alkyl derivatives thereof and/or N—$C_1$–$C_{12}$alkyl derivatives thereof such as, especially, dimethylaminoethanol and N,N,O-trimethylethanolamine.

D) Suitable solvents also include aromatic nitrogen heterocycles, for example pyridine and quinoline.

E) Suitable solvents are also especially carboxylic acid esters and amides and carbonic acid esters and amides of the general formulae $RCO(OR^2)$, $RCO(NR^3R^4)$, $O{=}C(OR^2)_2$, $O{=}C(OR^2)(NR^3R^4)$ and $O{=}C(NR^3R^4)_2$ wherein $R^2$ to $R^4$, in each case and each independently of any other(s), is a radical as defined above under A) and B). Solvents that are especially suitable are dimethylformamide (DMF) and tetramethylurea (TMU).

F) Suitable solvents are also especially cyclic carbonic acid derivatives of the general formula II,

(II)

wherein $R^2$ is a radical as defined above under A) and B), X is a C=O or C=$NR^3$ group, Y is an $NR^4$ group or an oxygen atom and A is an alkylene bridge —$[CR_2]_n$— wherein n=from 1 to 12. The radicals R, $R^2$, $R^3$, $R^4$, in each case and each independently of any other(s), are a radical as defined above under A) and B).

Suitable solvents are especially ethylene carbonate, propylene carbonate and 1,3-dimethyl-3,4,5,6-tetrahydro-2 (1H)-pyrimidinone (=dimethylpropyleneurea, DMPU).

The reaction with activated zinc is preferably carried out in the presence of an ethereal solvent, especially tetrahydrofuran, dioxane, dimethyl ether, diethyl ether, di(isopropyl) ether, methyl (tert-butyl) ether or 1,2-dimethoxyethane (DME).

Non-polar organic solvents suitable for process step (b) are, for example, arenes, such as benzene, toluene, o-, m- and p-xylene, 1,3,5-trimethylbenzene (mesitylene), ethylbenzene, diphenylethane, 1,2,3,4-tetrahydronaphthalene (Tetralin), isopropylbenzene (cumene), 1-methylnaphthalene and mixtures of such solvents.

Activated zinc is, for example, zinc powder, zinc dust or zinc granules, which have been activated chemically, thermally, electrochemically, with the aid of ultrasound or using one of the methods described in E. Erdik, *Tetrahedron*, 1987, 43, 2203–2212.

Zinc can be chemically activated by adding a small amount of $I_2$, a halogenated carbon compound, a halogenated silicon compound or $HgCl_2$. Electrochemical activation of zinc can be carried out by applying a cathode voltage. Thermal activation can be effected by heating zinc granules or powder in vacuo. Activation can also be effected by ultrasound.

Activators suitable for process step b) include, for example, ethers and polyethers, amines and polyamines, and aromatic N-heterocycles and carbonic acid derivatives.

Preferred ethers are THF, dioxane, methyl (tertbutyl) ether (MTBE) and, especially, 1,2-dimethoxyethane DME.

Preferred polyethers are diethylene glycol dimethyl ether, triethylene glycol dimethyl ether and tetraethylene glycol dimethyl ether.

Preferred amines are triethylamine, tributylamine, piperidine, morpholine, N-methylpiperidine and N-methylmorpholine.

Preferred polyamines are tetramethylethylenediamine (TMEDA) and pentamethylethylenediamine (PMDETA).

Preferred aromatic nitrogen heterocycles are pyridine and quinoline.

Preferred carbonic acid derivatives are dimethylformamide DMF, tetramethylurea TMU and 1,3-dimethyl-3,4,5, 6-tetrahydro-2(1H)-pyrimidinone (=dimethylpropyleneurea, DMPU).

Process step (a) is preferably carried out at room temperature and can be represented by the following scheme:

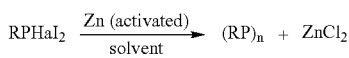
(1)

In that process step, advantageously zinc, which is dried beforehand in vacuo at approximately 200° C., is covered with a layer of the solvent, preferably tetrahydrofuran. Dihalo(organyl)phosphane is then added, whereupon an exothermic reaction occurs. The reaction product is worked up according to known methods customary in organic synthesis.

Process step (b) is carried out at temperatures in the range from −78° C. to 200° C. and can be represented by the following scheme:

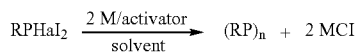
(2)

For that purpose, advantageously the metal M having a reducing action (M=Li, Na, K, Cs, Mg) is placed in a non-polar organic solvent in the presence of the activator and then the dihalo(organyl)phosphane is added. The reaction time is from 10 minutes to 8 hours. The reaction product is worked up according to known methods customary in organic synthesis.

The ratio by volume of non-polar solvent to activator is from 10:0.1 to 10:5, especially from 10:0.5 to 10:2.

The non-polar organic solvent is especially toluene and the activator is especially tetramethylethylenediamine or 1,2-dimethoxymethane.

Use of the metal in process step (b) in an amount exceeding the stoichiometric ratio enables novel di(alkali metal/alkaline earth metal) oligophosphanediides to be prepared.

The synthesis of the di(alkali metal/alkaline earth metal) oligophosphanediides proceeds in accordance with the schemes (3), (4) and (5):

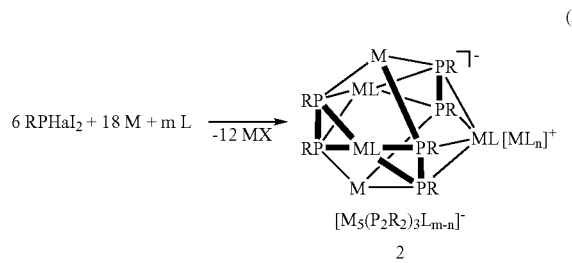
(3)

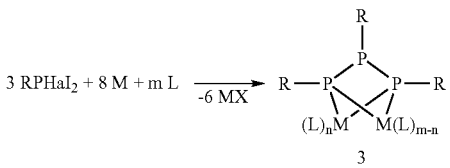
(4)

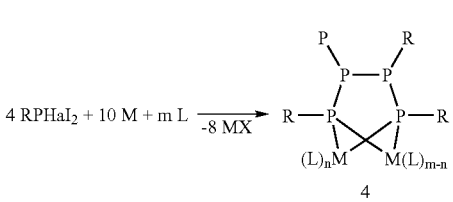
(5)

The invention relates also to di(alkali metal/alkaline earth metal) oligophosphanediides of formulae (2), (3) and (4)

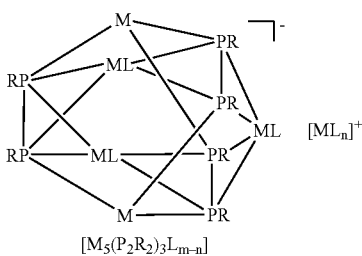

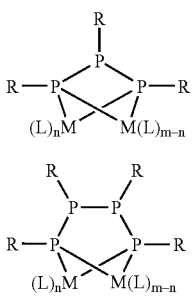

wherein
R is $C_1$–$C_6$alkyl; $C_3$–$C_6$cycloalkyl, aryl or heteroaryl;
M is Li, Na, K, Cs or Mg;
Hal is F, Cl, Br or I;
L is an activator; and
n and m denote the number of coordinated molecules L, which may be from 1 to 8.

Aryl and Heteroaryl are as defined under formula I.

The activator is preferably an ether or polyether, especially 1,2-dimethoxyethane (DME), or an amine or polyamine, especially tetramethylethylenediamine (TMEDA).

The preparation of the di(alkali metal/alkaline earth metal) oligophosphanediides of formulae (2) to (4) is carried out by reaction of dihalo(organyl)phosphanes of formula $RPHal_2$, wherein R is $C_1$–$C_{12}$alkyl; $C_3$–$C_{12}$cycloalkyl, aryl or heteroaryl,
Hal is F, Cl, Br or I, and
n is a number from 3 to 20, with an alkali metal or alkaline earth metal in a non-polar organic solvent in the presence of an activator, the molar ratio of alkali metal or alkaline earth metal to $RPHal_2$ being >1.

The di(alkali metal/alkaline earth metal) oligophosphanediides of formulae (2), (3) and (4) are suitable for the preparation of organophosphorus compounds.

In particular, [Na(tmeda)$_3$][Na$_5$(P$_2$Ph$_2$)$_3$(L)$_3$] (2A: L=TMEDA; 2B: L=DME) is suitable for the preparation of organophosphorus compounds in accordance with reaction equations (6) to (10) given in the following reaction scheme:

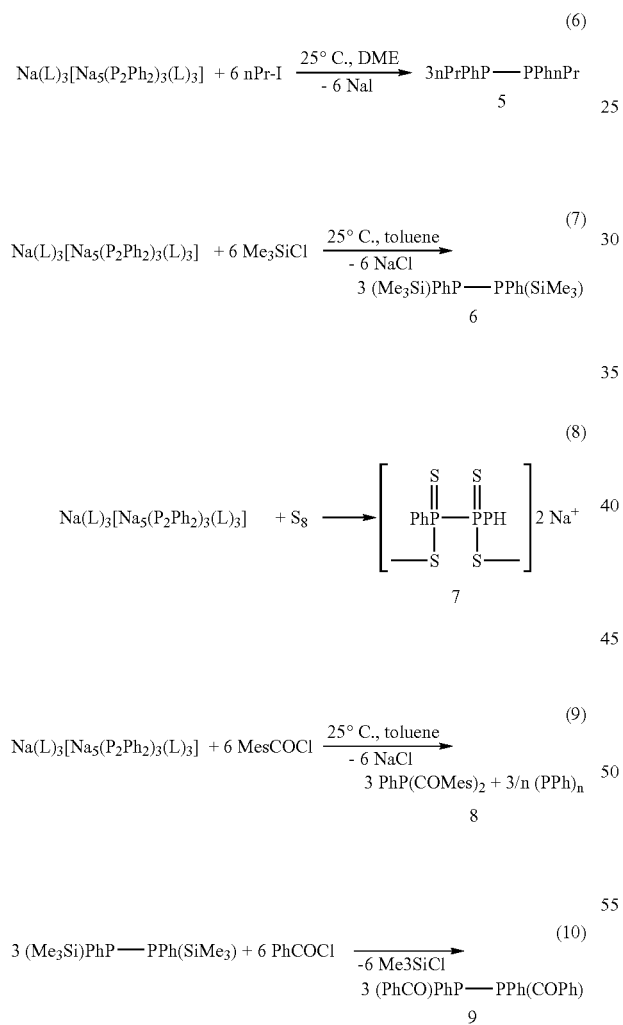

Accordingly, using alkyl halides such as n-propyl iodide, the diphosphane 5 is obtained in quantitative yield (in the form of a mixture of the R,S and R,R or S,S isomers).

Using trimethylsilyl chloride, $Me_3SiCl$, it is possible to prepare bisphenylbis(trimethylsilyl)diphosphane 6 in high yield, hitherto obtainable only by complex methods.

Using sulfur, the novel disodium salt of tetrathiohypodiphosphonic acid 7 is obtained in quantitative yield. Hitherto only the dilithium and dipotassium salts and also a nickel complex of the little investigated tetrathiohypodiphosphonic acid have been described. The maximum yield achieved was about 60%.

The reaction of 2 with arylcarboxylic acid chlorides, such as mesitoyl chloride, results, with disproportionation, in bis(mesitoyl)phenylphosphane 8 and cyclophenylphosphane, especially the cyclopentaphosphane 1 $(PhP)_5$.

Finally, bis(acyl)diphosphanes, such as bis(benzoyl)diphosphane 9, are obtainable from the bissilyldiphosphane 6 and equivalent amounts of the appropriate carboxylic acid chloride. Those compounds are also obtainable in a one-pot process by reaction of the disodium diphosphanediides 2 with $Me_3SiCl$ and subsequent addition of RCOCl.

The following Examples explain the invention in greater detail.

EXAMPLE 1

Preparation of Pentaphenylcyclopentaphosphane $(PhP)_5$

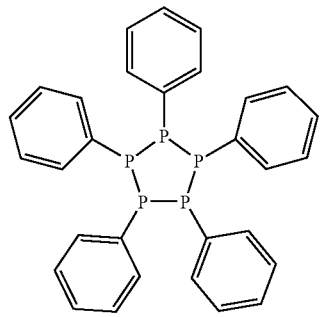

Process Variant a)

In a 150 ml Schlenk tube, 8.18 g of zinc powder (0.125 mol) are dried for 2 hours at approximately 200° C. under an oil pump vacuum. The cooled zinc powder is covered with a layer of 60 ml of anhydrous, oxygen-free THF. 17.0 ml of $PhPCl_2$ (0.125 mol) are slowly added dropwise, with vigorous stirring, in such a manner that the temperature of the reaction solution does not exceed 40° C. After stirring for a further 30 minutes at RT, the THF is distilled off under an oil pump vacuum. After taking up the light-yellow solid in 80 ml of $CH_2Cl_2$, the light-yellow suspension is washed twice with 25 ml of an aqueous saturated $NH_4Cl$ solution each time and is then dried over $Na_2SO_4$. The $CH_2Cl_2$ is distilled off under an oil pump vacuum and the colourless solid is recrystallised from a suitable solvent (e.g. $CH_3CN$, $Et_2O$).

Yield: 11.83 g (88%); $^{31}P$ NMR ($C_6D_6$): δ=–3.7 ppm (m); $(PhP)_4$ and $(PhP)_6$ each <2%.

EXAMPLE 2

Preparation of Pentaphenylcyclopentaphosphane $(PhP)_5$

Process Variant b)

160 ml (138 g) of toluene and 6.5 g of TMEDA (0.056 mol) are placed under a nitrogen atmosphere in a 500 ml Schlenk vessel. 2.53 g (0.110 mol) of sodium are added, which are melted by heating and suspended by stirring. After cooling the suspension to approximately 50° C., 10 g of PhPCl$_2$ (0.055 mol) are added thereto. The mixture is then heated for approximately 90 minutes at a bath temperature of 140° C. At the beginning of the reaction, the suspension becomes turbid and takes on a slightly brown-red colour; NaCl is precipitated during the reaction. The reaction mixture, which no longer contains any metal, is concentrated to dryness under a high vacuum and, with the exclusion of oxygen, 50 ml of saturated aqueous NH$_4$Cl solution are added to the residue and extraction is carried out with 100 ml of CH$_2$Cl$_2$. After concentration of the CH$_2$Cl$_2$ phase and drying under a high vacuum, slightly brownish pentaphenylcyclopentaphosphane remains. Yield: 5.28 g (89%), content of (PhP)$_6$ and (PhP)$_4$<5%

EXAMPLE 3

Preparation of a Disodium (Diphenyldiphosphanediide of Formula [Na(tmeda)$_3$][Na$_5$(P$_2$Ph$_2$)$_3$ (tmeda)$_3$] (2a) and [Na(dme)$_3$][Na$_5$(P$_2$Ph$_2$)$_3$(dme)$_3$] (2b)

100 ml of toluene and 15 ml of TMEDA are placed under a nitrogen atmosphere in a 500 ml Schlenk vessel. 3.86 g (0.168 mol) of sodium are added, which is melted by heating and suspended by stirring, and then, after cooling the suspension to approximately 50° C., 10.00 g of PhPCl$_2$ (0.055 mol) are slowly added thereto. The mixture is then heated for approximately 6 hours at a bath temperature of 140° C. (reflux). At the beginning of the reaction, the suspension becomes turbid and takes on a green and then a brown-red colour. The end of the reaction is indicated by the precipitation of a light-yellow residue 2a in the form of fine crystals and the supernatant solution is bright yellow-orange. The precipitated solid 2a is filtered off under a nitrogen atmosphere using a suction filter. It can be dissolved in dimethoxyethane or THF, separated from NaCl by filtration, and then crystallised in the form of bright-orange-coloured hexagonal prisms 2b by concentration of the solution. The composition and constitution of the compounds 2a as [Na (tmeda)$_3$][Na$_5$(P$_2$Ph$_2$)$_3$(tmeda)$_3$] and 2b as [Na(dme)$_3$][Na$_5$ (P$_2$Ph$_2$)$_3$(dme)$_3$] according to structure 2 in the formula drawing is confirmed by $^{31}$P, $^1$H-NMR spectroscopy, $^{23}$Na-MAS-NMR spectroscopy and by a single-crystal X-ray structural analysis of 2b.

2a, 2b: $^{31}$P NMR (121.49 MHz, [D$_8$]THF): δ=−106.4 (s); 2b: $^1$H NMR (300.13 MHz, [D$_8$]THF): δ=3.30 (s, 6H; dme, CH$_3$), 3.46 (s, 4H; dme, CH$_2$), 6.42 (app. t, 1H; p-Ph-H), 6.71 (app. t, 2H; m-Ph-H), 7.24 (app. d, 2H; o-Ph-H); $^{13}$C NMR (62.90 MHz, [D$_8$]THF): δ=59.8 (s; dme, CH$_3$), 73.6 (s; dme, CH$_2$), 119.0 (s; p-Ph-C), 127.8 (s; m-Ph-C), 131.1 (m; o-Ph-C), 160.7 (m; ipso-Ph-C); $^{23}$Na NMR (66.16 MHz, [D$_8$]THF): δ=32 (br. s, b$_{1/2}$=1300 Hz).

Crystal data of [Na(dme)$_3$][Na$_5$(P$_2$Ph$_2$)$_3$(dme)$_3$] 2b: hexagonal, a=15.04(2), b=15.04(2), c=20.93(4); α=90°, β=90°, γ=120°.

EXAMPLE 4

Preparation of a Disodium (Triphenyltriphosphanediide) of Formula Na$_2$(P$_3$Ph$_3$)(tmeda)$_3$ (3)

4.38 g (24.5 mmol) of PhPCl$_2$ are heated at reflux for from 6 to 7 hours with 1.50 g (65.3 mmol, 2.67 equivalents) of sodium in 70 ml of toluene and 10 ml of TMEDA and then insoluble products are removed by filtration. Disodium triphosphanediide [Na$_2$(P$_3$Ph$_3$)(tmeda)$_3$] is obtained in the form of an orange solid from the red solution by fractional crystallisation.

Alternatively, the triphosphanediide 3 can be prepared from 2 and 4 by a synproportionation reaction, giving a yield of from 60 to 70%.

$^{31}$P NMR (101.25 MHz, [D$_8$]THF): 8 lines–AB$_2$ spin system, δ$_A$=−54.0 (Ph-P), δ$_B$=−56.7, $^1$J$_{AB}$=242.4 Hz. $^1$H NMR (250.13 MHz, [D$_8$]THF): δ=2.15 (s, 36H; tmeda, CH$_3$), 2.30 (s, 12H; tmeda, CH$_2$), 6.35 (app. t, 2H; p-Ph-H, terminal), 6.67 (app. t, 4H; m-Ph-H, terminal)*, 6.76 (m, 1H; p-Ph-H, central), 6.88 (app. t, 2H; m-Ph-H, central)**, 7.46 (app. d, 4H; o-Ph-H, terminal)*, 7.72 (app. d, 2H; o-Ph-H, central)**; $^{13}$C NMR (62.90 MHz, [D$_8$]THF): δ=47.1 (s; tmeda, CH$_3$), 59.8 (s; tmeda, CH$_2$), 118.3 (s; p-Ph-C, terminal), 124.6 (s; p-Ph-C, central), 127.7 (m; m-Ph-C, terminal, central), 130.5 (m; o-Ph-C, terminal)*, 132.7 (m; o-Ph-C, central)*; 161.4 (m; ipso-Ph-C, central), 162.9 (m; ipso-Ph-C, terminal).

Crystal data of [Na$_2$(P$_3$Ph$_3$)(tmeda)$_3$]: monoclinic, a=10.500(1), b=14.914(1), c=27.046(1), β=91.890(4).

EXAMPLE 5

Preparation of a Disodium (Tetraphenyltetraphosphanediide) of Formula Na$_2$(P$_4$Ph$_4$)(tmeda)$_2$ (4a) and Na$_2$(P$_2$Ph$_4$)(dme)$_3$ (4b)

10.00 g (56 mmol) of PhPCl$_2$ are heated at reflux for from 6 to 7 hours with 3.21 g (140 mmol, 2.5 equivalents) of sodium in 100 ml of toluene and 15 ml of TMEDA and then filtered while hot. The disodium tetraphosphanediide [Na$_2$ (P$_4$Ph$_4$)(tmeda)$_2$] 4a is crystallised from the red solution in the form of a yellow solid in a yield of from 60 to 70%. Recrystallisation of (4a) using dimethoxyethane yields (4b).

$^{31}$P NMR (101.25 MHz, [D$_8$]THF, 298 K): δ=−24.2 (m, 2P, $^-$PPh-PPh-PPh-PPh$^-$, −70.0 (br, s, 1P, —PPh$^-$) −85.0 (br, s, 1P, -PPh$^-$); $^1$H NMR (250.13 MHz, [D$_8$]THF): δ=2.15 (s, 24H; tmeda, CH$_3$), 2.30 (s, 8H; tmeda, CH$_2$), 6.43 (app. t, 2H; p-Ph-H, terminal), 6.68 (app. t, 4H; m-Ph-H, terminal), 6.91 (app. t, 2H; p-Ph-H, central), 7.04 (app. t, 4H; m-Ph-H, central), 7.31 (app. d, 4H; o-Ph-H, terminal), 7.87 (br. s, 4H; o-Ph-H, central); $^{13}$C NMR (62.90 MHz, [D$_8$]THF): δ=47.1 (s; tmeda, CH$_3$), 59.8 (s; tmeda, CH$_2$), 119.8 (s; p-Ph-C, terminal), 125.9 (s; p-Ph-C, central), 127.8 (s; m-Ph-C, terminal), 128.4 (s; m-Ph-C, central), 131.0 (m; o-Ph-C, terminal), 133.5 (m; o-Ph-C, central), 151.5 (br.; ipso-Ph-C, central), 159.4 (br.; ipso-Ph-C).

Crystal data of [Na$_2$(P$_4$Ph$_4$)(tmeda)$_2$]: triclinic, a=10.17 (1), b=10.27(1), c=11.94(1); α=76.403(18)°, β=71.328 (16)°, γ=62.138(17)°.

EXAMPLE 6

Preparation of a Disodium (Diphenyldiphosphanediide) of Formula [Na$_2$P$_2$Ph$_2$(tmu)$_n$]$_m$ (n=0–10 and m=1–∞)

100 ml of toluene and 15 ml of N,N,N',N'-tetramethylurea (TMU) are placed under a nitrogen atmosphere in a 500 ml Schlenk vessel. 3.86 g (0.168 mol) of sodium are added, which is melted by heating and suspended by stirring, and then, after cooling the suspension to approximately 50° C., 10.00 g of PhPCl$_2$ (0.055 mol) are slowly added thereto. The mixture is subsequently heated for approximately from 3 to 4 hours at a bath temperature of 140° C. (reflux). The end of the reaction is indicated by the precipitation of a voluminous yellow solid, which is separated off under a nitrogen atmosphere using a suction filter. The solid consists of NaCl and pure $Na_2P_2Ph_2$ with a content, not ascertained in detail, of TMU. Unlike 2a,b, the substance is sparingly soluble in THF and is identified by $^{31}$P NMR and by derivatisation with trimethylsilyl chloride.

$^{31}$P NMR (121.49 MHz, $[D_8]$THF): δ=−106.0 (s);

After the addition of an excess of trimethylsilyl chloride at room temperature, there is formed with immediate decoloration and as the only product, $Ph_2P_2(Si[CH_3]_3)_2$: $^{31}$P NMR (121.49 MHz, $C_6D_6$): −107.4 (s).

What is claimed is:

1. A process for preparing a cycloorganylphosphane of formula I $(R^1P)_n$     I by reaction of a dihalo(organyl)phosphane of the formula $R^1PHal_2$,
wherein
$R^1$ is $C_1$–$C_{12}$alkyl; $C_3$–$C_{12}$cycloalkyl, aryl or heteroaryl,
Hal is F, Cl, Br or I, and
n is a number from 3 to 20,
with
a) activated zinc in an organic solvent, or with
b) sodium in a non-polar organic solvent in the presence of tetramethylethylenediamine, wherein the ratio by volume of non-polar solvent to tetramethylethylenediamine is from 10:0.1 to 10:5.

2. A process according to claim 1 for preparing a cycloorganylphosphane of formula I by reaction of a dihalo(organyl)phosphane of the formula $R^1PHal_2$ with activated zinc in an ethereal solvent.

3. A process according to claim 1 for preparing a cycloorganylphosphane of formula I by reaction of a dihalo(organyl)phosphane of the formula $R^1PHal_2$ with sodium in a non-polar organic solvent in the presence of tetramethylethylenediamine, wherein the ratio by volume of non-polar solvent to tetramethylethylenediamine activator is from 10:0.1 to 10:5.

4. A process according to claim 3 wherein the non-polar organic solvent is toluene.

5. A process according to claim 1 wherein $R^1$ is phenyl.

6. A di(alkali metal/alkaline earth metal) oligophosphanediide of the structural formula 2, 3 or 4

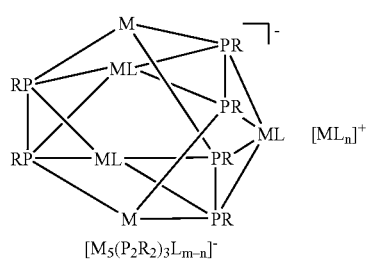

2

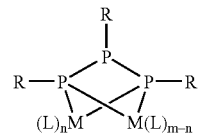

3

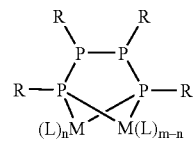

4 wherein

R is $C_1$–$C_6$alkyl; $C_3$–$C_6$cycloalkyl, aryl or heteroaryl;

M is Li, Na, K, Cs or Mg;

Hal is F, Cl, Br or I;

L is an activator; and n and m denote the number of coordinated molecules L, which may be from 1 to 8.

7. A di(alkali metal/alkaline earth metal) oligophosphanediide according to claim 6 wherein R is phenyl and L is tetramethylethylenediamine or 1,2-dimethoxyethane.

8. A process for the preparation of a di(alkali metal/alkaline earth metal) oligophosphanediide of formula (2), (3) or (4) according to claim 6 by reaction of a dihalo (organyl)phosphane of the formula $RPHal_2$, wherein R is $C_1$–$C_{12}$alkyl; $C_3$–$C_{12}$cycloalkyl, aryl or heteroaryl, Hal is F, Cl, Br or I, and n is a number from 3 to 20, with an alkali metal or alkaline earth metal in a non-polar organic solvent in the presence of an activator, wherein the molar ratio of alkali metal or alkaline earth metal to $RPHal_2$ is >1.

9. A process for the preparation of an organophosphorus compound by reaction of a di(alkali metal/alkaline earth metal) oligophosphanediide of formula (2), (3) or (4) according to claim 6 with an alkyl halide, trimethylsilyl chloride, sulfur, an arylcarboxylic acid chloride or trimethylsilyl choride and subsequently a carboxylic aicd chloride.

10. A process according to claim 2 wherein $R^1$ is phenyl.

11. A process according to claim 3 wherein $R^1$ is phenyl.

* * * * *